US011181199B2

(12) United States Patent
Fornarelli (10) Patent No.: US 11,181,199 B2
(45) Date of Patent: Nov. 23, 2021

(54) ASSEMBLY FOR PREVENTING LEAKAGE IN A VAPORIZATION DEVICE

(71) Applicant: 14TH ROUND INC., Los Angeles, CA (US)

(72) Inventor: Thomas Fornarelli, Chicago, IL (US)

(73) Assignee: 14TH ROUND INC., Los Angeles, CA (US)

( * ) Notice: Subject to any disclaimer, the term of this patent is extended or adjusted under 35 U.S.C. 154(b) by 223 days.

(21) Appl. No.: 16/431,595

(22) Filed: Jun. 4, 2019

(65) Prior Publication Data

US 2020/0383383 A1 Dec. 10, 2020

(51) Int. Cl.
*A24F 40/485* (2020.01)
*F16K 1/46* (2006.01)

(52) U.S. Cl.
CPC .............. *F16K 1/46* (2013.01); *A24F 40/485* (2020.01)

(58) Field of Classification Search
CPC ...... A24F 47/002; A24F 47/008; A24F 40/00; A24F 40/40; A24F 40/485; F16K 1/46
USPC .................................................. 131/328, 329
See application file for complete search history.

(56) References Cited

U.S. PATENT DOCUMENTS

| 8,997,754 | B2 | 4/2015 | Tucker et al. |
| 9,078,473 | B2 | 7/2015 | Worm et al. |
| 9,247,773 | B2 | 2/2016 | Memari et al. |
| 2013/0192623 | A1 | 8/2013 | Tucker et al. |
| 2014/0190503 | A1 | 7/2014 | Li et al. |
| 2014/0283825 | A1* | 9/2014 | Buchberger ...... A61M 15/0021 128/202.21 |
| 2014/0332019 | A1 | 11/2014 | Liu |
| 2014/0360514 | A1 | 12/2014 | Zhu |
| 2014/0360516 | A1 | 12/2014 | Liu |
| 2015/0144147 | A1 | 5/2015 | Li et al. |
| 2016/0007654 | A1 | 1/2016 | Zhu |
| 2016/0015082 | A1 | 1/2016 | Liu |
| 2016/0183597 | A1 | 6/2016 | Li et al. |
| 2016/0366943 | A1 | 12/2016 | Li et al. |
| 2017/0156408 | A1* | 6/2017 | Li ............................ H05B 3/16 |
| 2018/0000156 | A1* | 1/2018 | Qiu ......................... A24F 40/40 |

* cited by examiner

*Primary Examiner* — Hae Moon Hyeon
(74) *Attorney, Agent, or Firm* — Flener IP & Business Law; Zareefa B. Flener; Ayhan E. Mertogul (57) ABSTRACT

An assembly for preventing leakage in a vaporization device comprises an inner tube slidably supported within an outer tube, and a plate fixedly attached at a first end of the inner tube. A vaporization chamber having at least one aperture disposed therethrough is fixedly attached within the outer tube. A spring is disposed in a compressed state between the plate and an interior of the outer tube, and a cover is fixedly attached at a second end of the inner tube, the cover having a skirt. In a first state the plate is held by the compressive force of the spring at a first end of the outer tube so that the aperture is not covered by the skirt, and in a second state the plate is pushed into the outer tube by further compressing the spring so that the aperture is covered by the skirt.

20 Claims, 8 Drawing Sheets

ASSEMBLY FOR PREVENTING LEAKAGE IN A VAPORIZATION DEVICE

FIELD OF THE INVENTION

The invention is related to an assembly for preventing leakage in a vaporization device. More specifically, the assembly comprises a cover operable to either open or close at least one aperture of a vaporization chamber depending on whether in a first position or a second position.

BACKGROUND

Vaporization devices use electrical energy to heat a material to form an inhalable substance. In some example implementations, components of vaporization devices may be characterized as electronic cigarettes, and those electronic cigarettes most preferably incorporate tobacco or marijuana and/or components derived from tobacco or marijuana. Vaporization devices also can be characterized as being vapor-producing articles or medicament delivery articles. Thus, such articles or devices can be adapted so as to provide one or more substances (e.g., flavors and/or pharmaceutical active ingredients) in an inhalable form or state. Alternatively, inhalable substances can be in the form of an aerosol (i.e., a suspension of fine solid particles or liquid droplets in a gas). For purposes of simplicity, the term "vapor" as used herein is meant to include vapors, gases and aerosols of a form or type suitable for human inhalation, whether or not visible, and whether or not of a form that might be considered to be smoke-like.

Vaporization devices comprise some combination of a battery, at least one control component (such as a microprocessor, individually or as part of a microcontroller), a heating element (such as an electrical resistance heating element), a liquid chamber for holding a liquid capable of yielding a vapor upon application of sufficient heat, and a mouthpiece or tip for allowing a user to draw upon the vaporization device for inhalation of the vapor.

Some vaporization devices are reusable and other vaporization devices are disposable. In either case, if a user does not intend to use all the liquid in a liquid chamber in one use of the vaporization device, an assembly is needed to prevent leakage of a liquid from the liquid chamber to the vaporization chamber. Leakage of the liquid may cause damage to the heating element, the control component, or the battery. Additionally, the vaporization device can be jostled or be affected by barometric pressure changes that provide impetus for the liquid to leak out of the liquid chamber.

SUMMARY OF THE INVENTION

According to one aspect of the invention, an assembly for preventing leakage in a vaporization device comprises an inner tube slidably supported within an outer tube, and a plate fixedly attached at a first end of the inner tube, the plate constrained from moving out of the outer tube. A vaporization chamber is attached within the outer tube, the vaporization chamber having at least one aperture disposed therethrough. A spring is disposed in a compressed state between the plate and an interior of the outer tube, and a cover is fixedly attached at a second end of the inner tube, the cover having a skirt sized to surround the vaporization chamber. In a first state the plate is held by the compressive force of the spring at a first end of the outer tube so that the at least one aperture is not covered by the skirt, and in a second state the plate is pushed into the outer tube by further compressing the spring so that the at least one aperture is covered by the skirt.

According to another aspect of the invention an assembly for preventing leakage in a vaporization device comprises an inner tube slidably supported within an outer tube by a stopper disposed on a first ledge extending inwardly within the outer tube. A plate is fixedly attached at a first end of the inner tube, wherein the plate is constrained from moving out of the outer tube by having an outermost dimension that is larger than an inner dimension of a second ledge that extends inwardly within the outer tube. A vaporization chamber is attached within the outer tube, the vaporization chamber having at least one aperture disposed therethrough. A spring is disposed in a compressed state between the plate and the first ledge, and a cover is fixedly attached at a second end of the inner tube, the cover having a skirt sized to surround the vaporization chamber. In a first state the plate is held by the compressive force of the spring at a first end of the outer tube so that the at least one aperture is not covered by the skirt, and in a second state the plate is pushed into the outer tube by further compressing the spring so that the at least one aperture is covered by the skirt.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Figure 1:
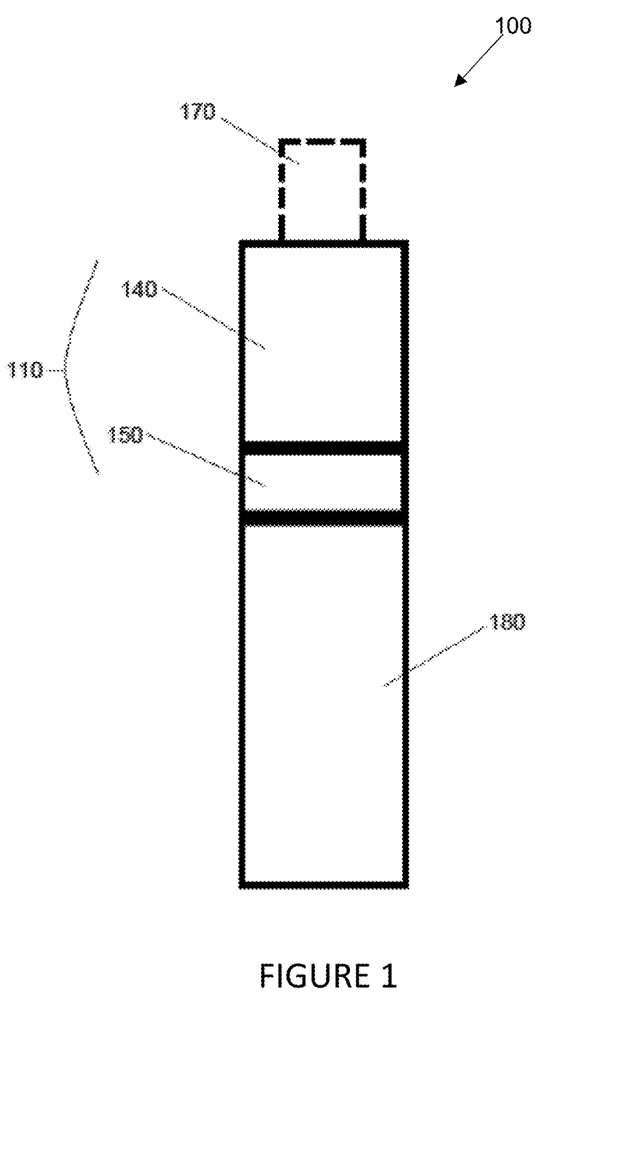
FIG. 1 illustrates a schematic view of an embodiment of a vaporization device.

FIG. 1 illustrates an embodiment of a vaporization device 100 having a disposable tank 140, a vaporization chamber 150, and a battery 180. In some embodiments, an assembly 110 includes both the tank 140 and the vaporization chamber 150. The vaporization chamber 150 may also be referred to as, for example, but not limited to, a vaporizer, an atomizer, a cartomizer, a clearomizer, and other terms known in the art. The assembly 110 accommodates a mouthpiece 170 at an end of the tank 140 opposite the vaporization chamber 150. The battery 180 includes an electrical power source and may also include, but is not limited to, a control component, a sensor, and a user feedback mechanism.

Figure 2:
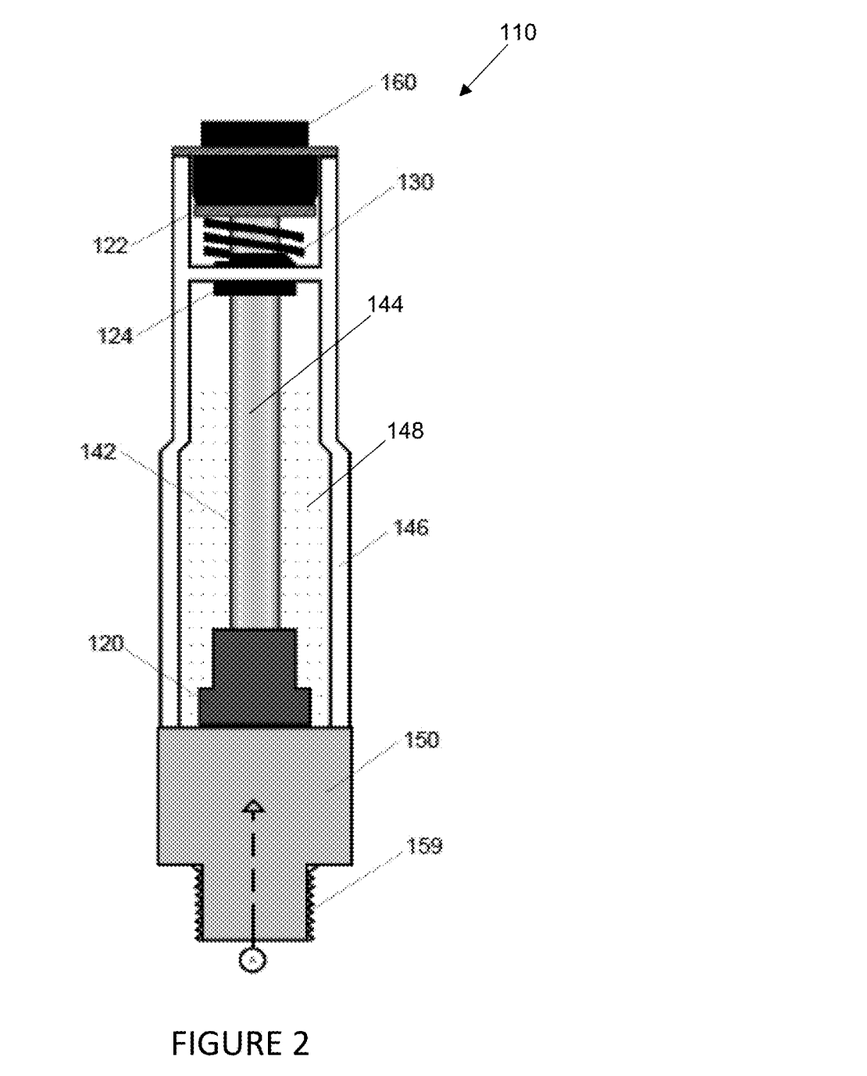
FIG. 2 illustrates an embodiment of a leakproof assembly within the vaporization device of FIG. 1.

FIG. 2 is an illustration of an embodiment of the assembly 110 of the vaporization device 100. The assembly 110 includes an outer tube 146, an inner tube 142, and a vaporization chamber 150. The inner tube 142 is slidably supported within the outer tube 146 and defines an airflow passage 144 therethrough. The outer tube 146 defines an outer boundary of a liquid chamber 148 disposed around the inner tube 142. The liquid chamber 148 holds vaporization liquid for supplying to the vaporization chamber 150. In one embodiment, the liquid chamber 148 is sized to hold, for example without limitation, 11.5 milliliters (ml) or 14 ml of vaporization liquid. The tubes 142, 146 are circular and concentric in this embodiment; however, in other embodiments the tubes 142, 146 are non-circular and/or non-concentric. In this embodiment, the outer tube 146 has a variable diameter along its length. In other embodiments, the outer tube 146 has a uniform diameter.

Figure 8:
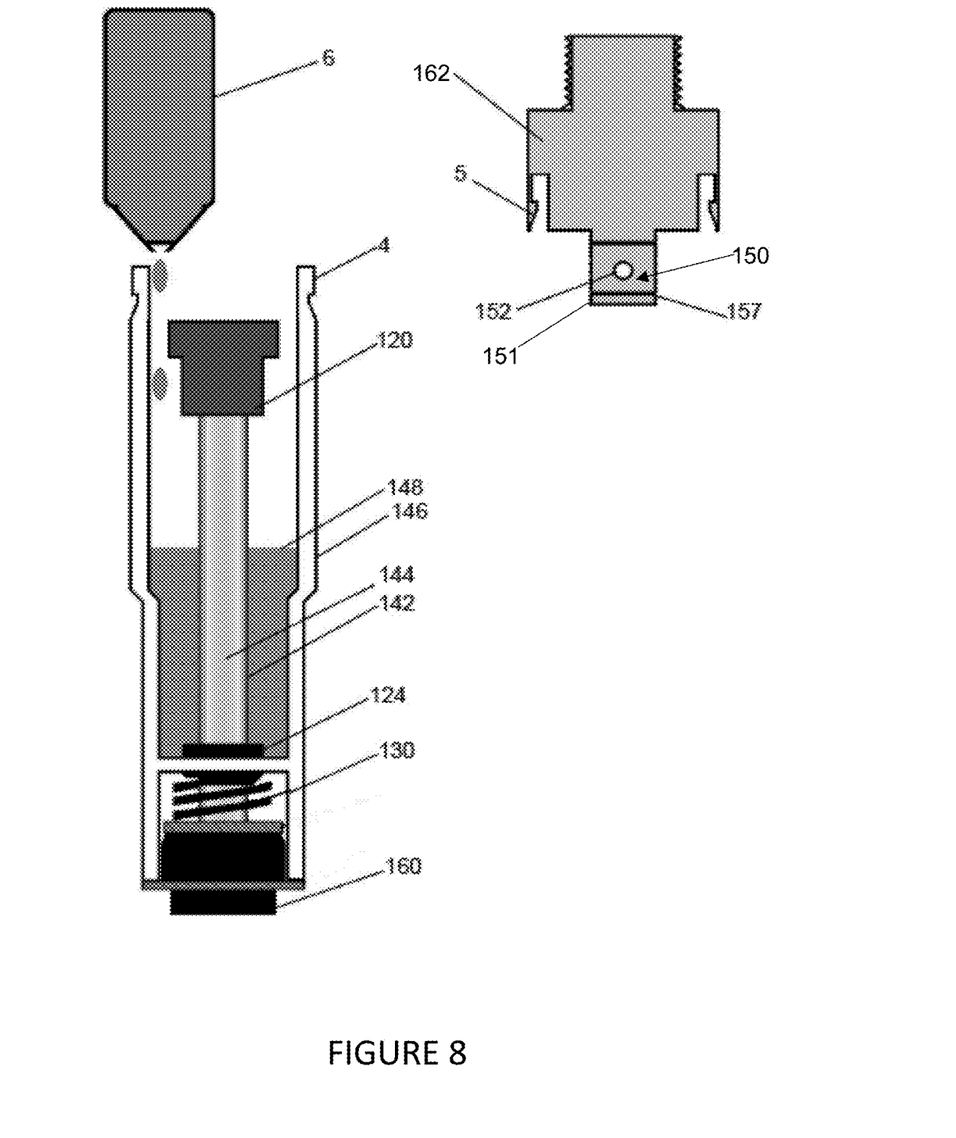
FIG. 8 illustrates filling the liquid chamber of the assembly.

The vaporization chamber 150 is fixedly attached within the outer tube 146, for example, via a snap fit of an inwardly facing protrusion or hook 5 on the vaporization chamber 150 over a shoulder or tab 4 on an outer surface of the outer tube 146 as shown in FIG. 8, via an adhesive, via threads, or via any suitable form of attachment as is known in the art. The vaporization chamber 150 includes a threaded portion 159 that receives the battery 180. In some embodiments, the vaporization chamber 150 includes a vaporization head 151 and a vaporization base 155 (as shown in FIG. 3), which may be detachably attached to each other.

The assembly 110 further includes a stopper 124, a spring 130, a cover 120, a top plate 122, and a removable cap 160. The stopper 124 slidably supports the inner tube 142 relative to the outer tube 146. Additionally, in some embodiments, the stopper 124 prevents liquid from passing between portions of the outer tube 146.

Figure 3:
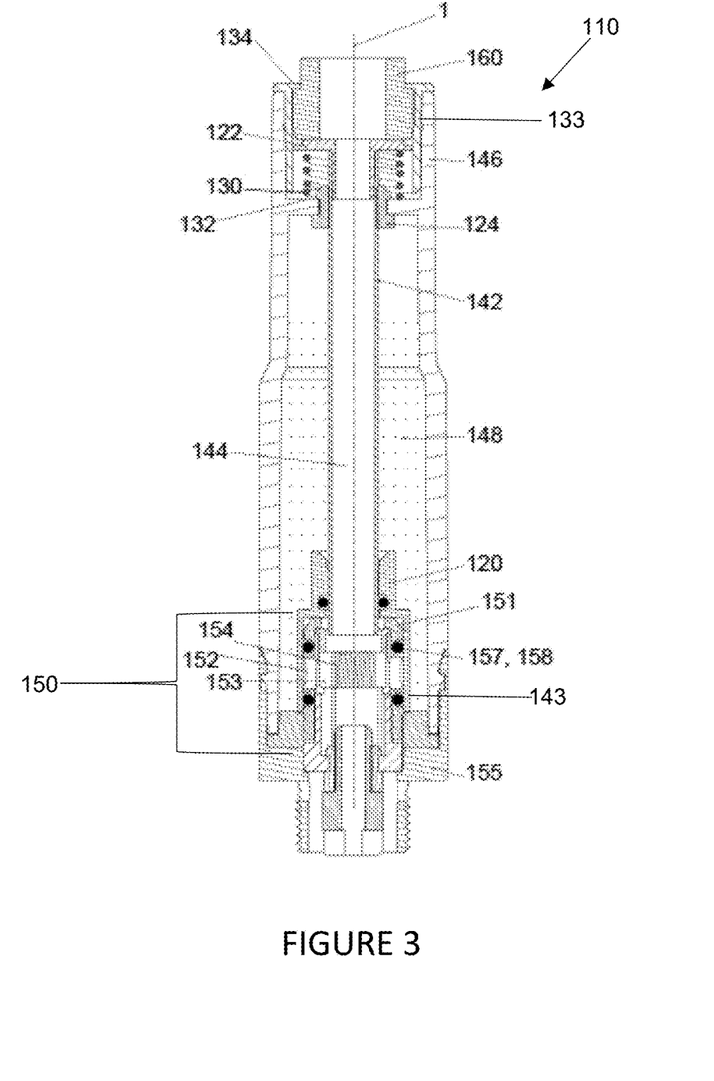
FIG. 3 illustrates a cross-sectional view of the assembly shown in a closed state.
Figure 4:
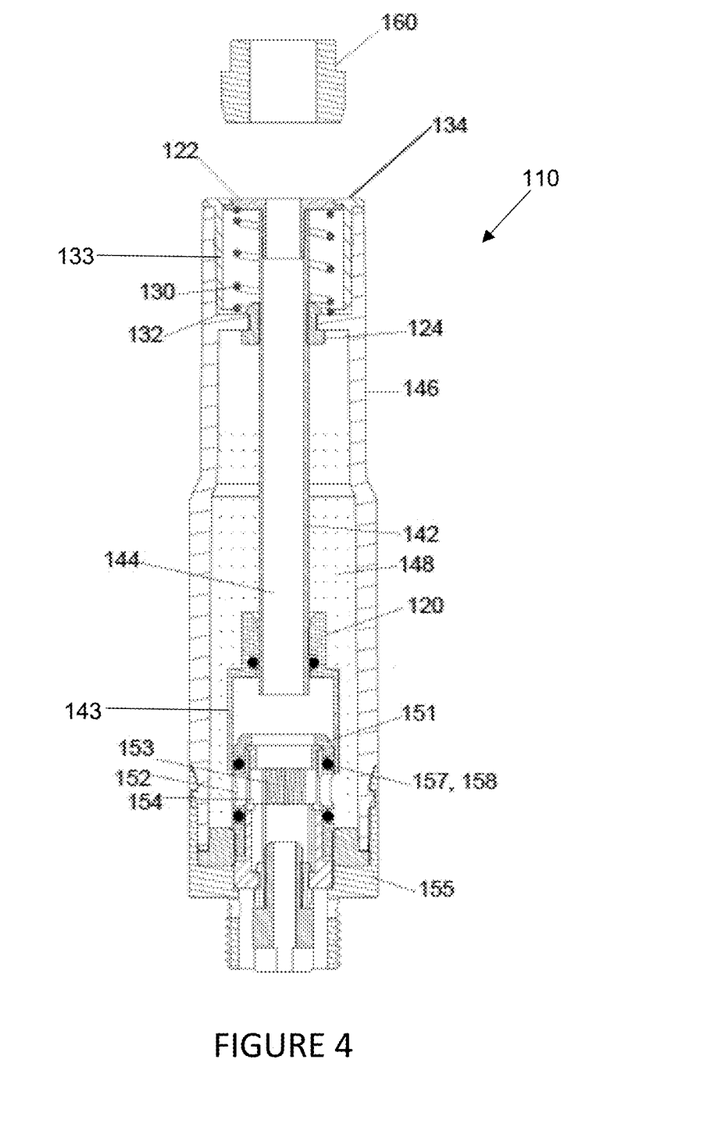
FIG. 4 illustrates a cross-sectional view of the assembly shown in an open state.

FIGS. 3 and 4 illustrate cross-sectional views of the assembly 110 of FIG. 2 taken along a line passing radially through a longitudinal axis 1. In one embodiment the top plate 122 includes an aperture disposed therethrough and is attached to a top end of the inner tube 142 so that the aperture communicates with the airflow passage 144. In another embodiment the top plate 122 includes an aperture disposed therethrough and is attached to a top end of the inner tube 142 so that the aperture accommodates the diameter of the inner tube 142. The cover 120 is fixedly attached to a bottom end of the inner tube 142. The top plate 122 and the cover 120 may be fixedly attached to the inner tube 142 by, for example without limitation, welding, adhesive, friction, or an O-ring matching a groove. For example, the cover 120 is depicted in FIG. 3 as attached to the inner tube 142 via O-ring matching a groove, and the top plate 122 is depicted in FIG. 3 as attached to the inner tube 142 by friction (a tight fit between components).

The top plate 122, the inner tube 142, and the cover 120 are operable to move axially along the longitudinal axis 1 of the assembly 110. The spring 130 is operable to move the inner tube 142 by engaging the top plate 122 as is further explained below. In some embodiments, the top plate 122, the inner tube 142, and the cover 120 are concentric. The cover 120 overlaps a portion of the vaporization chamber 150. The cap 160 is removably inserted into the outer tube 146 at an end of the outer tube 146 opposite of the vaporization chamber 150.

The inner tube 142 and the outer tube 146 may be composed of, for example without limitation, a glass, a plastic, a metal, an alloy, or a combination of this and other suitable materials known in the art. In a preferred embodiment, the outer tube 146 is composed of glass or clear plastic so that a user can see how much liquid is in the liquid chamber 148. In some embodiments, the outer tube 146 includes a scale to measure the volume of liquid inside the liquid chamber 148. In the preferred embodiment, the inner tube is composed of stainless steel or aluminum. The vaporization chamber 150 is composed of, for example without limitation, stainless steel, aluminum, or another suitable metal or alloy known in the art.

Referring to FIG. 3 the assembly 110 is shown in a first position where the spring 130 is compressed axially along the longitudinal axis 1, which results in the assembly 110 being in a closed state. The spring 130 may be compressed axially in response to a compressive force being applied axially thereto. In some embodiments, the assembly 110 may include more than one spring 130 arranged in a series or a parallel arrangement relative to the longitudinal axis 1 of the inner tube 142.

The vaporization chamber 150 includes a vaporization head 151 and a vaporization base 155. The head 151 includes at least one aperture 152, a wick 153, a heating element 154, and at least one groove 157. The cover 120 includes a skirt 143 that extends past an end of the inner tube 142. The skirt 143 has an inner dimension that is greater than an outermost dimension of the vaporization head 151. The skirt 143 is operable to move axially along the longitudinal axis 1 between the closed state (see FIG. 3) and an open state (see FIG. 4). In one embodiment the skirt 143 and the vaporization chamber 150 are cylindrical structures. In other embodiments the skirt 143 and the vaporization chamber 150 can have other shapes. In a preferred embodiment, the inner dimension of the skirt 143 is close enough to the outermost dimension of the vaporization chamber 150 so as to provide a sealing effect therebetween with the addition of an O-ring (e.g., O-ring 158) or other means for sealing between two sliding surfaces as known in the art.

When the assembly 110 is in the closed state, the inner tube 142 and the skirt 143 define an inner boundary of the liquid chamber 148. In the closed state the skirt 143 covers the at least one aperture 152. When the assembly 110 is in the open state as described more fully below with regard to FIG. 4, the inner boundary of the liquid chamber is defined by the inner tube 142, the skirt 143, and an exposed portion of the vaporization chamber 150 that is no longer covered by the skirt 143. Thus, the skirt 143 in the closed state prevents liquid from entering the vaporization chamber 150 from the liquid chamber 148. The at least one groove 157 receives at least one O-ring 158. The at least one groove 157 and the at least one O-ring 158 form a seal between the skirt 143 and the vaporization head 151. The seal so formed prevents any leakage of liquid from the liquid chamber 148 to the vaporization chamber 150.

Still referring to FIG. 3, the outer tube 146 further includes a first ledge 132 and a second ledge 134. The first ledge 132 extends inwardly within the outer tube 146. The second ledge 134 also extends inwardly within the outer tube 146. In one embodiment, the second ledge is disposed at an opening of the outer tube 146. In other embodiments, the second ledge 134 is disposed within the outer tube 146 at a predetermined distance from the opening. The second ledge 134 may be integral with the outer tube 146, or as shown in FIGS. 3 and 4 the second ledge 134 may be part of a support ring 133 that is fixedly held within the opening of the outer tube 146. The support ring 133 may be fixedly held within the outer tube 146 by any suitable method of attachment as may be known in the art, for example without limitation by adhesive, by threads, by brazing or soldering, or by other methods of attachment. The second ledge 134 is sized to have an inner dimension that is smaller than an outermost dimension on the top plate 122 so that engagement between the second ledge 134 and the top plate 122 constrains the top plate 122 from moving out of the outer tube 146.

The stopper 124 is disposed on the first ledge 132 to slidably support the inner tube 142 inside the outer tube 146. The spring 130 is disposed in a compressed state between the first ledge 132 and the top plate 122. To force the assembly 110 onto the closed state the cap 160 is inserted into the assembly 110 between the top plate 122 and the second ledge 134. The cap 160 includes a portion that engages with the second ledge 134 to prevent the cap 160 from being pushed out of the outer tube 146 by the compressive force of the spring 130. The cap 160 presses the top plate 122 toward the vaporization chamber 150 and further axially compresses the spring 130. Because the top plate 122 and the cover 120 are both attached to the inner tube 142, movement of the top plate 122 toward the vaporization chamber 150 causes the inner tube 142 and the cover 120 to also move toward the vaporization chamber 150. Therefore, when the cap 160 is inserted as shown in FIG. 3, the skirt 143 covers and seals over the at least one aperture 152 on the vaporization head 151 of the vaporization chamber 150.

The removable cap 160 can be composed of, for example without limitation, silicone or rubber. The cap 160 may be inserted into the assembly 110 of the vaporization device 100 during manufacturing so that the assembly 110 is in the closed state during shipping to prevent leakage. A user removes the cap 160 when ready to use the vaporization device 100.

FIG. 4 illustrates the assembly 110 in an open state where the cap 160 has been removed. When the cap 160 is so removed, the spring 130 partially axially decompresses to push the top plate 122 up towards the second ledge 134 until the top plate 122 is level with the second ledge 134. Because the top plate 122 and the cover 120 are both attached to the inner tube 142, movement of the top plate 122 away from the vaporization chamber 150 by the partial axial decompression of the spring 130 causes the inner tube 142 and the cover 120 to also move away from the vaporization chamber 150. Movement of the cover 120 results in the skirt 143 of the cover 120 no longer covering the at least one aperture 152. Uncovering the at least one aperture 152 transitions the assembly 110 from the closed state to the open state.

In the open state liquid from the liquid chamber 148 is able to enter the vaporization chamber 150. The liquid soaks the wick 153 and is heated by the heating element 154. The wick 153 and the heating element 153 may be placed at a top, a center, a bottom, or multiple locations within the vaporization head 151. Vapor produced by heating the liquid travels through the airway passage 144 from the vaporization chamber 150 to the top plate 122. The at least one groove 157 and the at least one O-ring 158 maintain a seal that prevents liquid from entering the airway passage 144; only vapor produced within the vaporization chamber 150 by heating the liquid entering through the at least one aperture 152 enters the airway passage 144.

Figure 5:
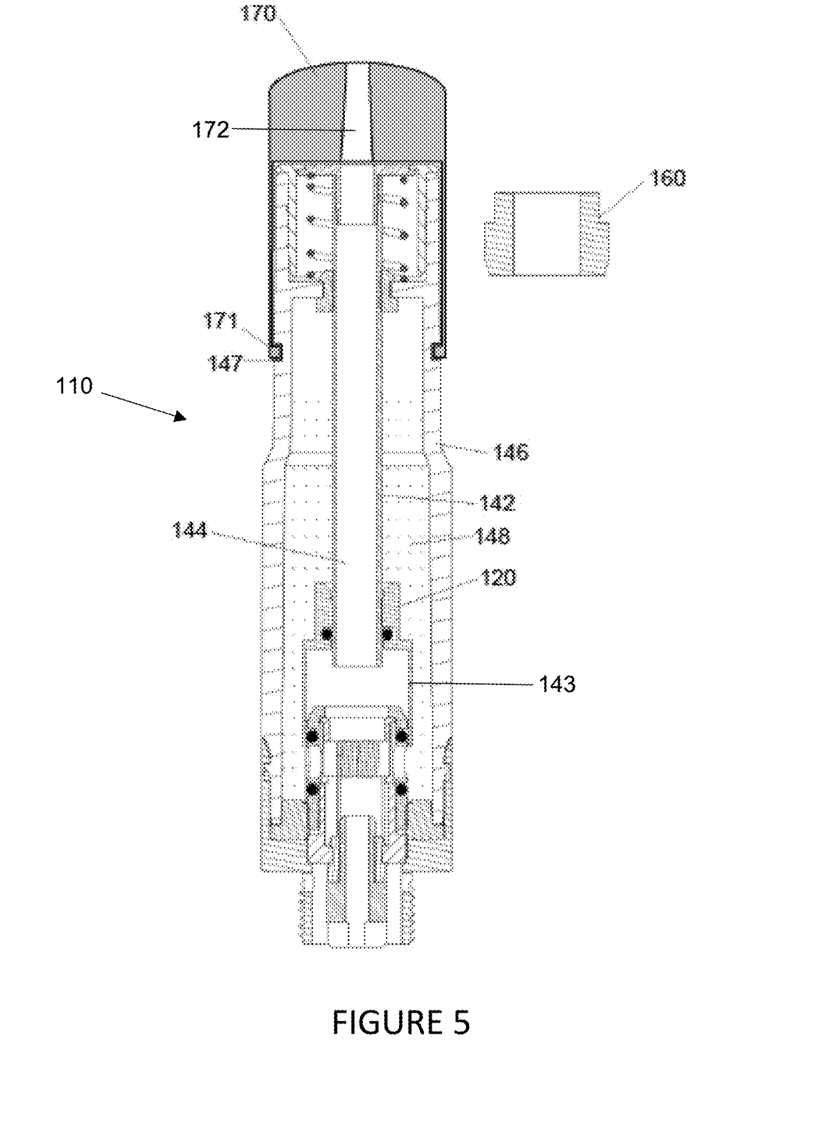
FIG. 5 illustrates a cross-sectional view of the assembly shown in an open state with a mouthpiece attached.

FIG. 5 illustrates an embodiment of the assembly 110 of FIG. 4 in the open state further including an attached optional mouthpiece 170. The mouthpiece 170 includes an orifice 172 through which a user may draw vapor from the vaporization device 100. The mouthpiece 170 may be attached to the assembly 110 as shown in FIG. 5 once the cap 160 is removed and the user is ready to inhale vapor produced by the vaporization chamber 150. When attached the mouthpiece 170 rests on the top plate 122 and the second ledge 134. An attaching lip 171 of the mouthpiece 170 is received by a receiving groove 147 disposed in an outer surface of the outer tube 146. In other embodiments no mouthpiece 170 is used; instead the user places their mouth directly over a top portion of the outer tube.

Figure 6:
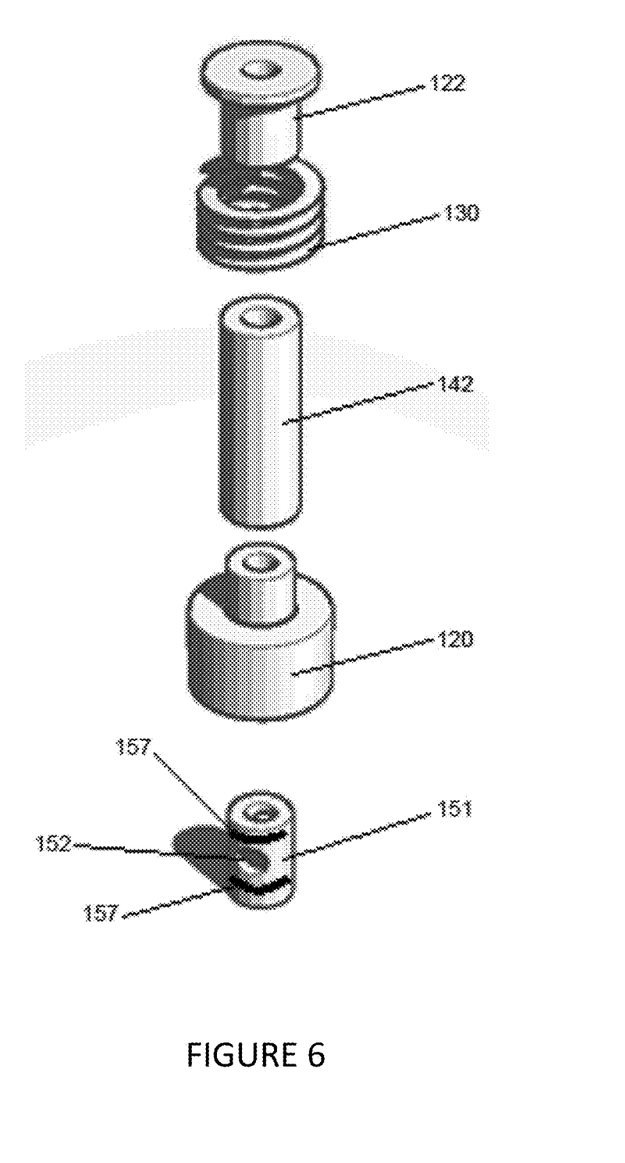
FIG. 6 illustrates an exploded view of some of the components of the assembly.

FIG. 6 illustrates an exploded view of components of an embodiment of the assembly 110 that operate to transition the assembly 110 between the closed and open states. In one embodiment the vaporization head 151 is removable from the vaporization base 155 and has two grooves 157 operable to receive two O-rings 158 (see O-ring 158 in FIG. 4). As previously described with respect to FIGS. 3 and 4, the grooves 157 and O-rings 158 provide a seal between the cover 120 and the head 151 to prevent passage of liquid from the chamber 148 into the vaporization chamber 150 when the assembly 110 is in the closed state and to further provide a seal between the cover 120 and the head 151 to prevent passage of liquid from the chamber 148 into the airway passage 144 when the assembly 110 is in the open state. The spring 130 is operable to move the cover 120 between the closed state and the open state by compressing and releasing compression. The spring 130 is disposed between the top plate 122 and the first ledge 132 (see FIGS. 3 and 4) of the outer tube 146.

Figure 7:
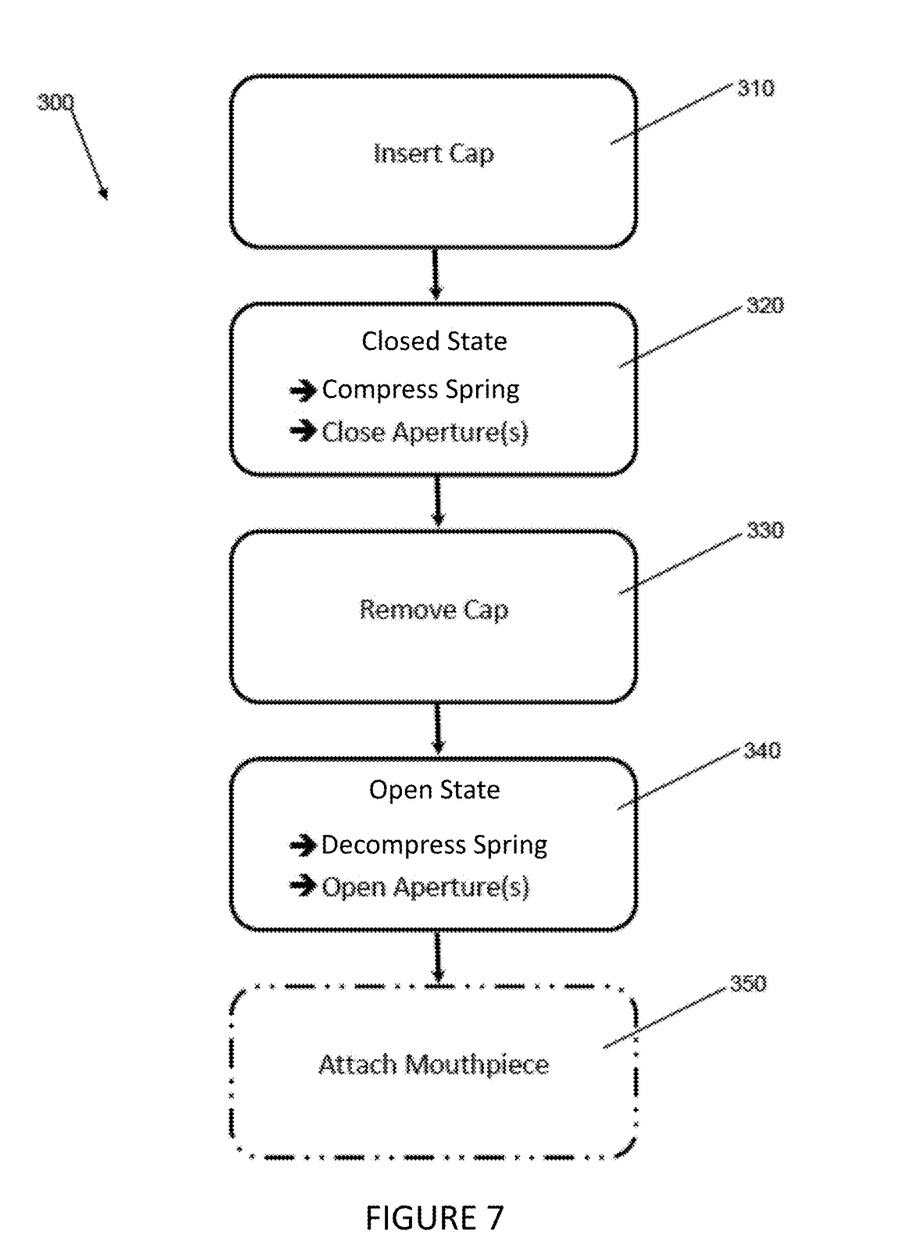
FIG. 7 illustrates a flowchart for a method of use of the assembly.

FIG. 7 illustrates a flowchart of a process 300 for using the assembly 110 of the vaporization device 100. At step 310, the cap 160 is inserted into the assembly 110, for example, by a manufacturer. As shown in FIG. 3, the cap 160 is inserted to be held between the top plate 122 and the second ledge 134. The insertion of the cap 160 at step 310 causes the assembly 110 to transition at step 320 from the open state to the closed state as has been described above. At step 330, a user removes the cap 160 causing the assembly 110 to transition at step 340 to the open state as has been described above. Optionally, at step 350 the user can further attach the mouthpiece 170 as shown in FIG. 5.

FIG. 8 illustrates how a manufacturer or a user may fill the liquid chamber 148 of the assembly 110, and how in one embodiment the vaporization chamber 150 may be removably attached to the outer tube 146. To fill the liquid chamber 148 the assembly 110 is inverted with the vaporization chamber 150 removed. Liquid is released from a bottle 6 so that the liquid is guided into the liquid chamber 148 avoiding the cover 120, and the airway passage 144. The stopper 124 prevents the liquid from entering past the first ledge 132. In some embodiments, the cap 160 is inserted prior to releasing the liquid. In other embodiments, the cap 160 is inserted after releasing the liquid from the bottle 6 but before reattaching attaching the vaporization chamber 150 so that the assembly 110 is maintained in the closed state.

In the embodiment shown in FIG. 8, a removable vaporization assembly 162 has the vaporization chamber 150 with the at least one aperture 152 and the at least one groove 157. Additionally, in one embodiment the removable vaporization assembly 162 includes one or more inwardly facing protrusions or hooks 5. The hooks 5 are operable to engage one or more shoulders or tabs 4 on an outer surface of the outer tube 146. The removable vaporization assembly 162 can be removed by simply disengaging the hooks 5 from the tabs 4. When the removable vaporization assembly 162 is attached to the outer tube 146, the vaporization head 151 is inserted into and covered by the cover 120. In some embodiments, the assembly 110 is disposable and meant only to be filled once by the manufacturer. In other embodiments, where the assembly 110 is reusable and can be refilled by a user, the removable vaporization assembly 162 can be removed to provide access to refilling the liquid chamber 148.

Those skilled in the art will appreciate that the invention described herein is susceptible to variations and modifications other than those specifically described, and that each embodiment is also provided with features that may be applicable to other embodiments. It is to be understood that the invention includes all such variations and modifications that fall within its spirit and scope. The invention also includes all the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. The exclusive rights to all modifications which come within the scope of the appended claims are reserved. All patents, patent publications and applications, and other references cited herein are incorporated by reference herein in their entirety.

INDUSTRIAL APPLICABILITY

An assembly for preventing leakage in a vaporization device comprises an inner tube slidably supported within an outer tube. A vaporization chamber is attached within the outer tube, and a compressed spring holds the assembly in a first open state allowing vaporization fluid from a liquid chamber to enter the vaporization chamber. A cap is inserted to further compress the spring and transition the assembly into a closed state where vaporization liquid is not allowed to enter the vaporization chamber. The assembly can be manufactured in industry and used by consumers.

I claim:

1. An assembly for preventing leakage in a vaporization device, the assembly comprising:
   an inner tube slidably supported within an outer tube by a stopper disposed on a first ledge extending inwardly within the outer tube;
   a plate fixedly attached at a first end of the inner tube, the plate constrained from moving out of the outer tube;
   a vaporization chamber attached within the outer tube, the vaporization chamber having at least one aperture disposed therethrough;
   a spring disposed in a compressed state between the plate and an interior of the outer tube; and
   a cover fixedly attached at a second end of the inner tube, the cover having a skirt sized to surround the vaporization chamber; wherein
      in a first state the plate is held by the compressive force of the spring at a first end of the outer tube so that the at least one aperture is not covered by the skirt; and
      in a second state the plate is pushed into the outer tube by further compressing the spring so that the at least one aperture is covered by the skirt.

2. The assembly of claim 1, wherein the plate is constrained from moving out of the outer tube by having an outermost dimension that is larger than an inner dimension of a second ledge that extends inwardly within the outer tube.

3. The assembly of claim 1, wherein the vaporization chamber is fixedly attached within the outer tube by an inwardly facing protrusion operable to engage a shoulder on an outer surface of the outer tube.

4. The assembly of claim 1, wherein the spring is disposed in a compressed state between the plate and the first ledge extending inwardly within the outer tube.

5. The assembly of claim 1 further comprising a liquid chamber disposed within the outer tube.

6. The assembly of claim 5, wherein when in the first state vaporization liquid from the liquid chamber can enter the vaporization chamber.

7. The assembly of claim 5, wherein when in the second state vaporization liquid from the liquid chamber cannot enter the vaporization chamber.

8. The assembly of claim 1, wherein the plate is pushed into the outer tube by a cap inserted between the plate and a second ledge that extends inwardly within the outer tube.

9. The assembly of claim 1 further comprising a removable mouthpiece that attaches to the outer tube.

10. The assembly of claim 1, wherein the vaporization chamber is part of a removable vaporization assembly.

11. A method for filling the assembly of claim 10, the method comprising the steps of:
    removing the removable vaporization assembly;
    inverting the assembly;
    delivering liquid into the liquid chamber; and
    reattaching the removable vaporization assembly.

12. The method of claim 11 further comprising the step inserting a cap between the plate and a second ledge that extends inwardly within the outer tube.

13. An assembly for preventing leakage in a vaporization device, the assembly comprising:
    an inner tube slidably supported within an outer tube by a stopper disposed on a first ledge extending inwardly within the outer tube;
    a plate fixedly attached at a first end of the inner tube, wherein the plate is constrained from moving out of the outer tube by having an outermost dimension that is larger than an inner dimension of a second ledge that extends inwardly within the outer tube;
    a vaporization chamber attached within the outer tube, the vaporization chamber having at least one aperture disposed therethrough;
    a spring disposed in a compressed state between the plate and the first ledge; and
    a cover fixedly attached at a second end of the inner tube, the cover having a skirt sized to surround the vaporization chamber; wherein
       in a first state the plate is held by the compressive force of the spring at a first end of the outer tube so that the at least one aperture is not covered by the skirt; and
       in a second state the plate is pushed into the outer tube by further compressing the spring so that the at least one aperture is covered by the skirt.

14. The assembly of claim 13, wherein the vaporization chamber is fixedly attached within the outer tube by an inwardly facing protrusion operable to engage a shoulder on an outer surface of the outer tube.

15. The assembly of claim 13 further comprising a liquid chamber disposed within the outer tube.

16. The assembly of claim 15, wherein when in the first state vaporization liquid from the liquid chamber can enter the vaporization chamber.

17. The assembly of claim 15, wherein when in the second state vaporization liquid from the liquid chamber cannot enter the vaporization chamber.

18. The assembly of claim 13, wherein the plate is pushed into the outer tube by a cap inserted between the plate and the second ledge.

19. The assembly of claim 13, wherein the vaporization chamber is part of a removable vaporization assembly.

20. An assembly for preventing leakage in a vaporization device, the assembly comprising:

an inner tube slidably supported within an outer tube;

a plate fixedly attached at a first end of the inner tube, the plate constrained from moving out of the outer tube;

a vaporization chamber attached within the outer tube, the vaporization chamber having at least one aperture disposed therethrough;

a spring disposed in a compressed state between the plate and an interior of the outer tube; and a cover fixedly attached at a second end of the inner tube, the cover having a skirt sized to surround the vaporization chamber; wherein in a first state the plate is held by the compressive force of the spring at a first end of the outer tube so that the at least one aperture is not covered by the skirt;

in a second state the plate is pushed into the outer tube by further compressing the spring so that the at least one aperture is covered by the skirt; and wherein the plate is pushed into the outer tube by a cap configured to be inserted between the plate and a second ledge that extends inwardly within the outer tube.

\* \* \* \* \*